United States Patent [19]

Fusegawa et al.

[11] Patent Number: 5,534,112
[45] Date of Patent: *Jul. 9, 1996

[54] METHOD FOR TESTING ELECTRICAL PROPERTIES OF SILICON SINGLE CRYSTAL

[75] Inventors: Izumi Fusegawa; Hirotoshi Yamagishi; Nobuyoshi Fujimaki; Yukio Karasawa, all of Gunma-ken, Japan

[73] Assignee: Shin-Etsu Handotai Co., Ltd., Tokyo, Japan

[ * ] Notice: The term of this patent shall not extend beyond the expiration date of Pat. No. 5,386,796.

[21] Appl. No.: 238,722

[22] Filed: May 5, 1994

Related U.S. Application Data

[63] Continuation of Ser. No. 796,385, Nov. 22, 1991.

[30] Foreign Application Priority Data

Nov. 22, 1990 [JP] Japan ................... 2-320467

[51] Int. Cl.$^6$ ................................ H01L 21/306
[52] U.S. Cl. ................ 156/662.1; 437/8; 437/10; 148/DIG. 60; 148/DIG. 162; 117/932
[58] Field of Search ............... 437/8, 10; 148/DIG. 60, 148/DIG. 162; 156/662; 117/932

[56] References Cited

U.S. PATENT DOCUMENTS

| | | | |
|---|---|---|---|
| 3,997,368 | 12/1976 | Petroff et al. | 148/188 |
| 4,539,050 | 9/1985 | Kramler et al. | 437/119 |
| 4,787,997 | 11/1988 | Saito et al. | 156/657 |
| 4,956,153 | 9/1990 | Yamagishi et al. | 117/217 |
| 5,386,796 | 2/1995 | Fusegawa et al. | 117/13 |

FOREIGN PATENT DOCUMENTS

| | | |
|---|---|---|
| 3223664 | 12/1983 | Germany. |
| 52-122479 | 10/1977 | Japan. |
| 60-146000 | 8/1985 | Japan. |
| 63-215041 | 9/1988 | Japan. |

OTHER PUBLICATIONS d'Aragena, "Dislocation Etch for (100) Planes in Silicon", J. Electrochen Soc. Solid State Science and Technology Jul. 1972 pp. 948–950.

Ghandhi, *VLSI Fabrication Principles, Silicon and Gellium Arsenide*, John Wiley & Sons, New York 1983 pp. 479–482 and 517–520.

Ehara Y., et al., "Correlation Between Discharge Magnitude Distribution and Luminescence Distribution Due to Electrical Treeing", Conference on Electrical Insulation and Dielectric Phenomena, 31–Oct.–1990, pp. 313–318.

*Primary Examiner*—Robert Kunemund
*Attorney, Agent, or Firm*—Ronald R. Snider

[57] ABSTRACT

The evaluation of the oxide film dielectric breakdown voltage of a silicon semiconductor single crystal is caried out by cutting a wafer out of the single crystal rod, etching the surface of the wafer with the mixed solution of hydrofluoric acid and nitric acid thereby relieving the wafer of strain, then etching the surface of the wafer with the mixed solution of $K_2Cr_2O_7$, hydrofluoric acid, and water thereby inducing occurrence of pits and scale-like patterns on the surface, determining the density of the scale-like patterns, and computing the oxide film dielectric breakdown voltage by making use of the correlating between the density of scale-like patterns and the oxide film dielectric breakdown voltage. This fact established the method of this invention to be capable of effecting an evaluation equivalent to the evaluation of the oxide film dielectric breakdown voltage of a PW wafer prepared from the single crystal rod.

2 Claims, 3 Drawing Sheets

METHOD FOR TESTING ELECTRICAL PROPERTIES OF SILICON SINGLE CRYSTAL

This is a continuation of application Ser. No. 07/796,385 filed Nov. 22, 1991 pending.

BACKGROUND OF THE INVENTION

1. Field of the Invention

This invention relates to a method for testing electrical properties of a silicon single crystal and more particularly to a method for evaluating dielectric breakdown voltage of the silicon oxide film grown on the surface of a polished wafer derived from the Czochralski (CZ) method or the floating zone (FZ) method by subjecting the single crystal derived therefrom to chemical treatments and visual inspection.

2. Description of the Prior Art

Heretofore, as means for evaluating the quality of a silicon semiconductor single crystal rod which has been pulled up by the Czochralski method or the floating zone pulling method, the so-called evaluation of oxide film dielectric breakdown voltage which comprises preparing a silicon polished wafer (PW wafer) from the single crystal rod, causing the silicon wafer to form an oxide film on the surface thereof, attaching a polysilicon electrode to the silicon wafer, applying a bias voltage thereto, and determining the dielectric breakdown voltage of the oxide film has been practised. This method has been recognized as one of the important testing techniques because it permits substantially equivalent simulation of the formation of a device on a silicon wafer and allows determination of the question as to whether or not the wafer manifests a suitable quality during the manufacture of a device using the wafer.

The evaluation of oxide film dielectric breakdown voltage mentioned above, however, entails such problems as (1) inability to effect this evaluation until after the PW wafer has been prepared, (2) inevitable consumption of enormous time during the process of evaluation, and (3) necessitation of an expensive apparatus for evaluation, for example.

This invention has as an object thereof the provision of a method which is capable of quickly and inexpensively effecting equivalent evaluation of the oxide film dielectric breakdown voltage of a wafer cut out of a given grown semiconductor single crystal without requiring preparation of a PW wafer for the evaluation.

The other objects and characteristic features of the present invention will become apparent to those skilled in the art as the disclosure is made in the following description of a preferred embodiment of the invention, as illustrated in the accompanying drawings.

SUMMARY OF THE INVENTION

The objects described above are accomplished by this invention providing a method for testing electrical properties of a silicon single crystal, characterized by pulling up a silicon semiconductor single crystal by the Czochralski method or the floating zone pulling method, cutting a wafer of a prescribed thickness from the single crystal, etching the surface of the wafer with a mixed solution of hydrofluoric acid and nitric acid thereby relieving the wafer of strain, then selectively etching the surface of the wafer in a mixed solution of $K_2Cr_2O_7$, hydrofluoric acid, and water, and taking count of the number of scale-like patterns consequently appearing on the surface of the wafer thereby evaluating the silicon single crystal.

DETAILED DESCRIPTION OF THE PREFERRED EMBODIMENT

For the evaluation by the method described above, the wafer is desired to have a thickness not less than 0.3 mm and not more than 2 mm. In order for the surface of this wafer to be smoothly and flatly etched, the ratio of hydrofluoric acid to nitric acid in the mixed solution is desired to be approximately 1:3. The selective etching of the wafer in the mixed solution of $K_2Cr_2O_7$, hydrofluoric acid, and water is desired to be carried out by keeping the wafer immersed in the mixed solution at normal room temperature for a period in the range of from 10 to 60 minutes.

As the mixed solution of $K_2Cr_2O_7$, hydrofluoric acid, and water, the SECCO solution [F. Secco D'Aragona: "J. Electrochem. Soc., 119 (1972), 948] has found popular recognition. The composition of the SECCO solution is obtained by dissolving $K_2Cr_2O_7$ in a proportion of 0.15 mol in water and mixing the resultant aqueous solution with an aqueous 49% hydrofluoric acid solution to a volumetric ratio of 1:2. The SECCO solution has been used for the purpose of selectively etching a heat-treated OSF (oxidation induced stacking fault) thereby producing a line defect image or for the purpose of visualizing a slippage suffered to occur in an ingot during the growth of the ingot. The use of this SECCO solution in visualizingscale-like patterns on a wafer as contemplated by this invention has never been known to the art.

Figure 1:
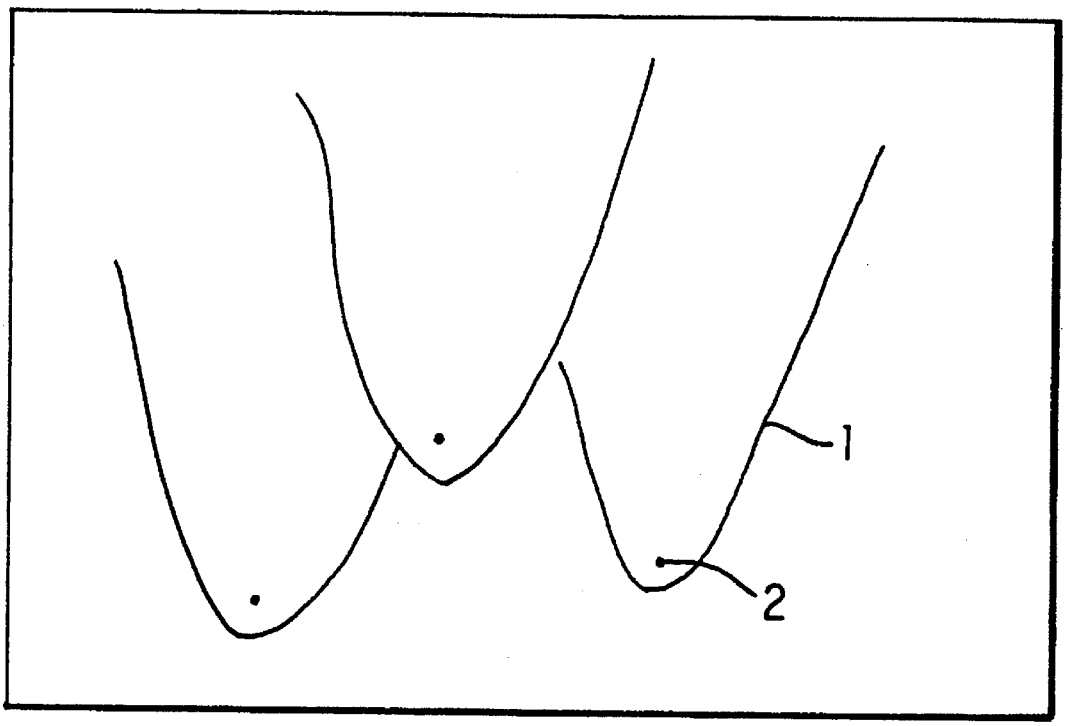
FIG. 1 is a sketch diagram of scale-like patterns formed on the surface of a silicon wafer when the silicon wafer has been subjected to mirror etching and then to etching with a SECCO solution.

The production of scale-like patterns is accomplished by cutting a wafer from a grown silicon semiconductor single crystal rod, subjecting the surface of the wafer to mirror etching with the mixed solution of hydrofluoric acid and nitric acid, and then further subjecting the resultant mirror surface of the wafer to etching with the mixed solution of $K_2Cr_2O_7$, hydrofluoric acid, and water. One example of a surface forming such scale-like patterns is illustrated in FIG. 1. A deliberate observation of this surface under an optical microscope reveals the presence of a minute pit 2 at the peak of each scale-like pattern 1. These scale-like patterns 1 are liable to generate such a gas as hydrogen at the portions of the pits 2. They occur as signs of uneven etching when the gas escapes upwardly. This fact is evinced by the phenomenon that these scale-like patterns are expanded upwardly in the vertical direction when the wafer is set upright in the liquid. It is inferred, however, that; the scale-like patterns originate in a certain kind of crystalline defect inherent in a crystal. The scale-like patterns formed by the etching of the wafer cut from the grown silicon semiconductor single crystal rod with the mixed solution of $K_2Cr_2O_7$, hydrofluoric acid, and water are found by examination to possess a density difference. This density difference is satisfactorily correlated with the oxide film dielectric breakdown voltage which is determined of a plurality of PW wafers. This fact established the method of this invention to be capable of effecting an evaluation equivalent to the evaluation of the oxide film dielectric breakdown voltage of a PW wafer prepared from the single crystal rod.

The evaluation of the oxide film dielectric breakdown voltage of a silicon semiconductor single crystal is carried out by cutting a wafer out of the single crystal rod immediately after its growth, etching the surface of the wafer with the mixed solution of hydrofluoric acid and nitric acid thereby relieving the wafer of strain, then etching the surface of the wafer with the mixed solution of $K_2Cr_2O_7$, hydrofluoric acid, and water thereby inducing occurrence of pits and scale-like patterns on the surface, determining the density of the scale-like patterns, and computing the oxide film dielectric breakdown voltage by making use of the correlating between the density of scale-like patterns and the oxide film dielectric breakdown voltage.

EXAMPLE

Now, the present invention will be described more specifically below with respect to working examples.

A plurality of silicon semiconductor single crystal rods 130 mm in diameter were pulled up, some by the CZ method and others by the FZ method. In the case of the CZ method, a quartz crucible 45 cm in diameter was used and the material placed therein was doped with boron and adjusted to an electric resistance coefficient of 10 $\Omega$cm. In all the single crystal rods pulled up by this method, the orientation was invariably <100>. In pulling up the silicon semiconductor single crystal rods by the case of the CZ method, the speed of pulling was varied from one batch to another between 0.4 mm/min to 1.7 mm/min. Incidentally, it is well known that the desirability of the oxide film dielectric breakdown voltage decreases in accordance as the pulling speed increases.

Figure 2:
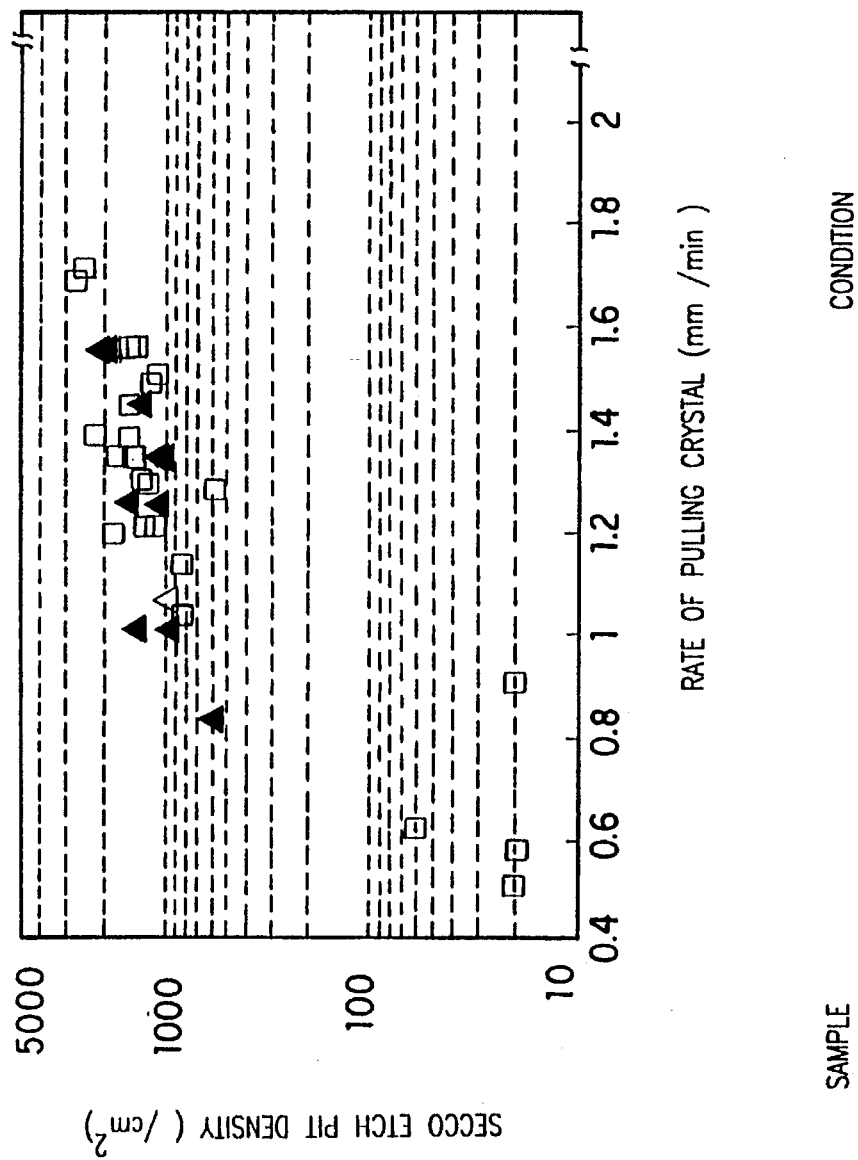
FIG. 2 is a graph showing the density of scale-like patterns formed on the surface of a CZ silicon wafer when the silicon wafer has been subjected to mirror etching and then to etching with a SECCO solution (SECCO etch pit density) as a function of the rate of pulling the crystal.

From each of the silicon single crystal rods produced by the pulling, silicon wafers 1 mm in thickness were sliced with a diamond saw and used as test pieces. Such a silicon wafer was subjected to mirror etching with the aforementioned mixed solution of hydrofluoric acid and nitric acid, washed thoroughly with purified water, and subjected to selective etching with the SECCO solution for a period in the range of from 1 to 60 minutes. On the test pieces etched for periods exceeding 10 minutes, scale-like patterns illustrated in FIG. 1 were observed extending upwardly in the vertical direction which the wafers were set upright in the solution. On the test pieces etched for periods exceeding 60 minutes, the formed scale-like patterns overlapped and consequently defied efforts in taking count of the density thereof. The wafer etched with the aforementioned liquid for 30 minutes, a period empirically found to be just fit, was placed under an optical microscope for the operator to take count of the density of scale-like patterns. The data of density thus obtained were plotted on a graph as a function of the speed of crystal growth. The results are shown in FIG. 2. In FIG. 2, the count of scale-like patterns was represented in the SECCO pit density. It is clearly noted from the graph that the SECCO pit density increased in accordance as the speed of crystal growth increased.

From the CZ silicon semiconductor single crystal rods mentioned above, PW wafers were prepared. The surfaces of these PW wafers were etched similarly with the SECCO solution and tested for SECCO etch pit density. The density distribution consequently obtained of these wafers was equal to that obtained of the wafers prepared from the aforementioned grown single crystal rods. This fact establishes the method of this invention to be capable of measuring the SECCO etch pit density without requiring the subsequent preparation of PW wafers.

Figure 3:
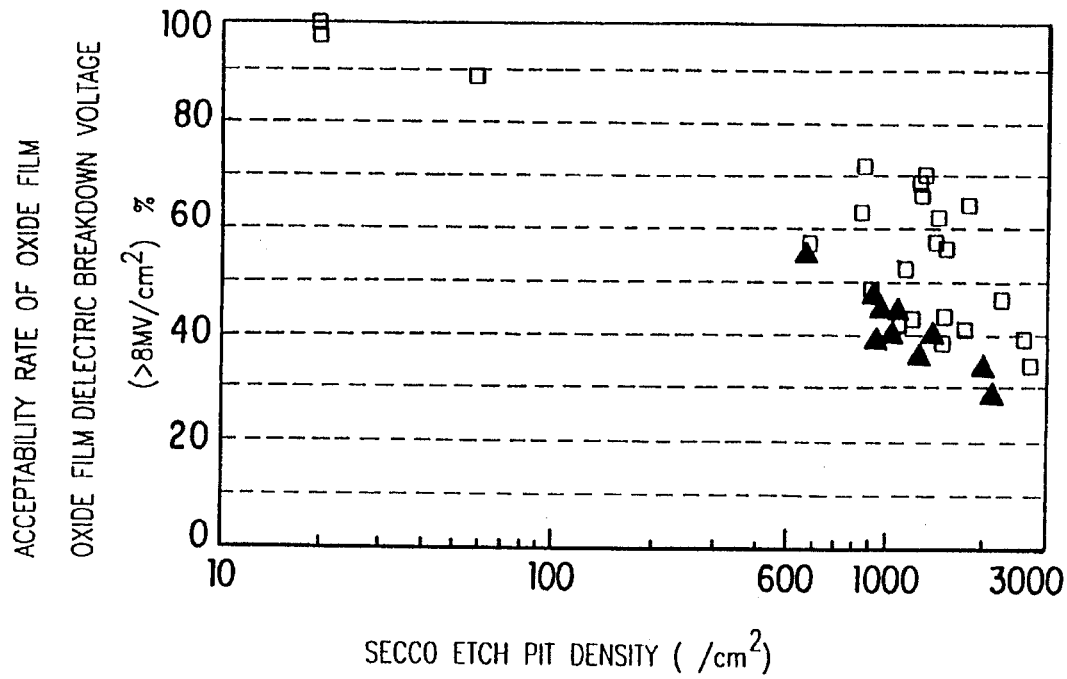
FIG. 3 is a graph showing the density of scale-like patterns formed on the surface of a CZ silicon wafer when the CZ silicon wafer has been subjected to mirror etching and then to etching with a SECCO solution (SECCO etch pit density) as a function of the acceptability rate of oxide film dielectric breakdown voltage %.

For the purpose of investigating the correlation between the SECCO etch pit density of such a wafer and the oxide film dielectric breakdown voltage, the PW wafers were subjected to a heat treatment in preparation for determination of the oxide film dielectric breakdown voltage. The wafers resulting from the heat treatment were cleaned with a RCA detergent and then subjected to gate oxidation at 900° C. for 100 minutes to form an oxide film 25 nm in thickness. On the oxide film-coated wafers, polysilicon was deposited and phosphorus was diffused to form an electrode pattern 8 $mm^2$ in area. For the measurement of the dielectric breakdown voltage of the oxide film, a voltage was applied to form an electric field of several MV/cm between the electrode and the silicon substrate. The level of voltage at which an electric current of not less than 1 $mA/cm^2$ began to flow was defined as the dielectric breakdown voltage. The wafers exhibiting not less than 8 MV/cm of oxide film dielectric breakdown voltage were rated as nonrejectable. The proportion nonrejectable was obtained by dividing the number of nonrejectable chips found in one PW wafer by the total number of chips formed in the same PW wafer and multiplying the quotient by 100. FIG. 3 shows the SECCO etch pit density as a function of the proportion nonrejectable represented in oxide film dielectric breakdown voltage (%). The two magnitudes involved herein showed a clear correlation such that the desirability of the oxide film dielectric breakdown voltage decreases in accordance as the SECCO etch pit density increased.

When wafers taken from the FZ silicon semiconductor single crystal rod were subjected to the same test, it was found that entirely the same correlation existed between the SECCO etch pit density and the oxide film dielectric breakdown voltage. In accordance with the method of this invention, therefor, the oxide film dielectric breakdown voltage property of a grown silicon semiconductor single crystal rod for the SECCO etch pit density without necessitating preparation of PW wafers and subsequent evaluation of the oxide film dielectric breakdown voltage thereof. This fact proves the effectiveness of this invention in the evaluation of interest.

In accordance with the present invention, a silicon semiconductor single crystal rod grown from molten silicon by the Czochralski method or the floating zone method can be given an evaluation equivalent to the evaluation of the oxide film dielectric breakdown voltage, one of the electrical properties, of a silicon wafer simply by cutting a wafer of a prescribed thickness from the single crystal rod instead of elaborately preparing silicon polished wafers from the single crystal rod, etching the surface of the wafer with the mixed solution of hydrofluoric acid and nitric acid thereby relieving the wafer of strain, then etching the surface with the mixed solution of $K_2Cr_2O_7$, hydrofluoric acid, and water for a prescribed length of time, and taking count of scale-like patterns consequently produced on the surface. This invention, therefore, obviates the necessity for spending time and labor in the preparation of the polished wafer, alloting time to the attendant step for evaluation, and installing an expensige device for evaluation and permits an evaluation equivalent to the evaluation of the oxide film dielectric breakdown voltage to be carried out quickly and inexpensively the use of a wafer cut out of the grown silicon semiconductor single crystal rod.

What is claimed is:

1. A method for testing electrical properties of a silicon single crystal comprising:

(a) pulling up a silicon semiconductor single crystal by the Czochralski method or the floating zone pulling method, cutting a wafer from said single crystal, etching the surface of the wafer with a mixed solution of hydrofluoric acid and nitric acid thereby relieving said wafer of strain, selectively etching the surface of the wafer in a mixed solution of $K_2Cr_2O_7$, hydrofluoric acid, and water without agitation, and counting the number of scale-like patterns consequently appearing on the surface of the wafer;

(b) obtaining a correlation of the number of scale-like patterns to the acceptability rate of oxide film dielectric breakdown voltage, wherein the number of scale-like patterns is obtained, independent of the step (a), by the same selective etching technique as recited in the step (a) with respect to a plurality of wafers; and (c) evaluating the acceptability of oxide film dielectric breakdown voltage from the number of scale-like patterns counted in the step (a) on the basis of said correlation obtained in the step (b).

2. The method for testing electrical properties of a silicon single crystal according to claim 1, wherein said single crystal wafer is relieved of strain by etching in said mixed solution of $K_2Cr_2O_7$, hydrofluoric acid, and water for 10 to 60 minutes.

\* \* \* \* \*